US005753265A

United States Patent [19]
Bergstrand et al.

[11] Patent Number: 5,753,265
[45] Date of Patent: May 19, 1998

[54] MULTIPLE UNIT PHARMACEUTICAL PREPARATION

[75] Inventors: Pontus John Arvid Bergstrand, Gothenburg; Kurt Ingmar Lövgren, Mölndal, both of Sweden

[73] Assignee: Astra Aktiebolag, Sodertalje, Sweden

[21] Appl. No.: 464,774

[22] PCT Filed: Jun. 7, 1995

[86] PCT No.: PCT/SE95/00678

§ 371 Date: Jun. 22, 1995

§ 102(e) Date: Jun. 22, 1995

[87] PCT Pub. No.: WO96/01624

PCT Pub. Date: Jan. 25, 1996

[30] Foreign Application Priority Data

Jul. 8, 1994 [SE] Sweden .................. 9402431-2

[51] Int. Cl.⁶ .................. A61K 9/28; A61K 9/30; A61K 9/34
[52] U.S. Cl. .................. 424/474; 424/475; 424/476; 424/477; 424/479; 424/480; 424/481; 424/482
[58] Field of Search .................. 424/474, 475, 424/476, 477, 479, 480, 481, 482

[56] References Cited

U.S. PATENT DOCUMENTS

| 4,853,230 | 8/1989 | Lovgren et al. | 424/468 |
|---|---|---|---|
| 4,927,640 | 5/1990 | Dahlinder et al. | 424/468 |

FOREIGN PATENT DOCUMENTS

| 0005129 | 4/1981 | European Pat. Off. |
|---|---|---|
| 0080341 | 6/1983 | European Pat. Off. |
| 0166287 | 1/1986 | European Pat. Off. |
| 0174726 | 3/1986 | European Pat. Off. |
| 0247983 | 12/1987 | European Pat. Off. |
| 0365947 | 5/1990 | European Pat. Off. |
| 0519144 | 12/1992 | European Pat. Off. |
| 2163747 | 3/1986 | United Kingdom |
| 9006925 | 6/1990 | WIPO |
| 9119712 | 12/1991 | WIPO |
| 9222284 | 12/1992 | WIPO |
| 9501783 | 1/1995 | WIPO |
| 9601623 | 1/1996 | WIPO |
| 9601624 | 1/1996 | WIPO |
| 9601625 | 1/1996 | WIPO |

OTHER PUBLICATIONS

Pharmaceutical Research, vol. 10 (1993), p. S–274.
Drugs Made in Germany, 37, No. 2 (1994), pp. 53–60.
Aulton M. E. (Churchill Livingston) Pharmaceutics: The Science of Dosage Form Design (1988), pp. 316–321.

*Primary Examiner*—Thurman K. Page
*Assistant Examiner*—Sharon Howard
*Attorney, Agent, or Firm*—White & Case

[57] ABSTRACT

A new pharmaceutical multiple unit tableted dosage form containing as active ingredient an acid labile $H^+K^+$-ATPase inhibitor or an alkaline salt thereof or one of its single enantiomers or an alkaline salt thereof, a method for the manufacture of such a formulation, and the method of treatment with such a formulation in medicine.

23 Claims, No Drawings

MULTIPLE UNIT PHARMACEUTICAL PREPARATION

FIELD OF THE INVENTION

The present invention is related to new pharmaceutical preparations in the form of a multiple unit tableted dosage form comprising an active substance in the form of an acid labile $H^+K^+$-ATPase inhibitor. The novel tableted dosage form is intended for oral use. Furthermore, the present invention refers to a method for the manufacture of such preparations and, to the use of such preparations in medicine.

BACKGROUND OF THE INVENTION

Acid labile $H^+K^+$-ATPase inhibitors also named as gastric proton pump inhibitors are for instance compounds known under the generic names omeprazole, lansoprazole, pantoprazole, pariprazole and leminoprazole.

Compounds of interest for the novel tableted dosage form according to the present invention are compounds of the general formula I or an alkaline salt thereof or one of its single enantiomers or an alkaline salt thereof.

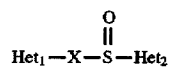

wherein
Het$_1$ is

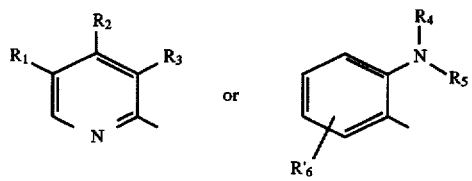

Het$_2$ is

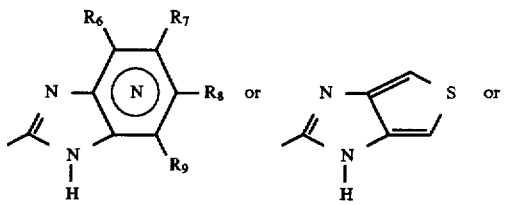

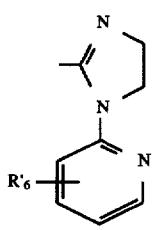

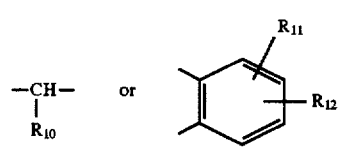

wherein
N in the benzimidazole moiety means that one of the carbon atoms substituted by $R_6$—$R_9$ optionally may be exchanged for a nitrogen atom without any substituents;

$R_1$, $R_2$ and $R_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;

$R_4$ and $R_5$ are the same or different and selected from hydrogen, alkyl and aralkyl;

$R_6'$ is hydrogen, halogen, trifluoromethyl, alkyl and alkoxy;

$R_6$—$R_9$ are the same or different and selected from hydrogen, alkyl, alkoxy, halogen, halo-alkoxy, alkylcarbonyl, alkoxycarbonyl, oxazolinyl, trifluoroalkyl, or adjacent groups $R_6$—$R_9$ form ring structures which may be further substituted;

$R_{10}$ is hydrogen or forms an alkylene chain together with $R_3$ and $R_{11}$ and $R_{12}$ are the same or different and selected from hydrogen, halogen or alkyl except the compounds 5-methoxy-2[[(4-methoxy-3,5-dimethyl-2-pyridinyl)methyl]sulfinyl]-1H-benzimidazole, 5-fluoro-2[[(4-cyclopropylmethoxy-2-pyridinyl)methyl]sulfinyl]-1H-benzimidazole and 5-carbomethoxy-6-methyl-2-[[(3,4-dimethoxy-2-pyridinyl)-methyl]sulfinyl-1H-benzimidazole.

Examples of specifically interesting compounds according to formula I are

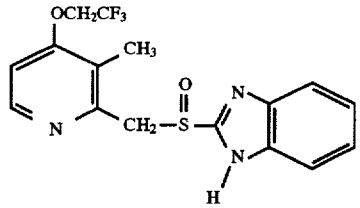

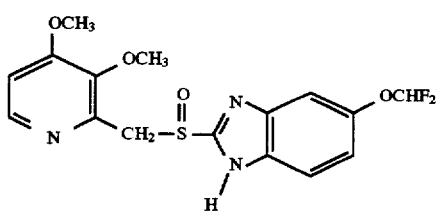

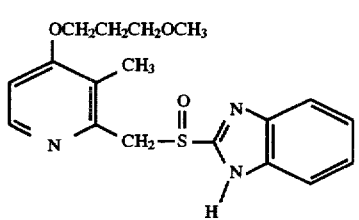

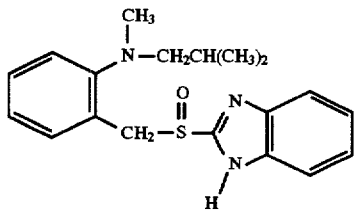

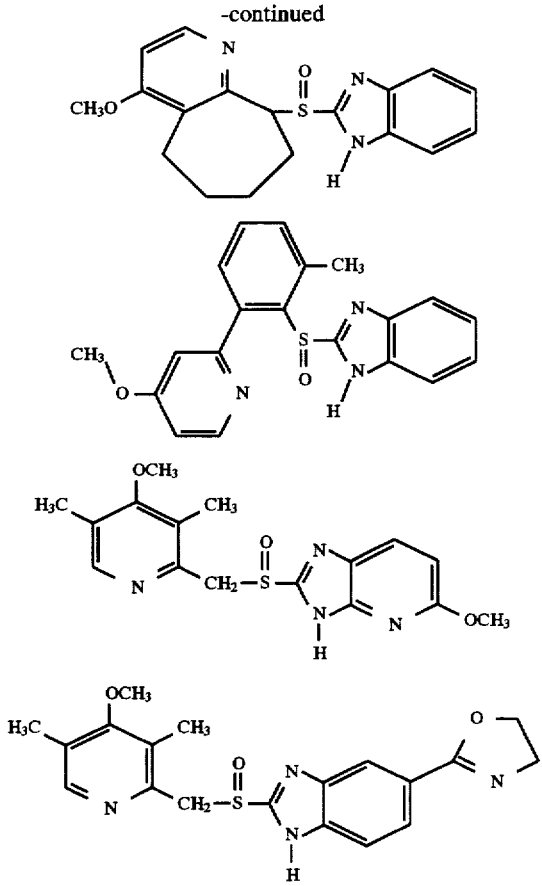

The active compound used in the tableted dosage form according to the invention may be used in neutral form or in the form of an alkaline salt, such as for instance the $Mg^{2+}$, $Ca^{2+}$, $Na^+$ or $K^+$ salts, preferably the $Mg^{2+}$ salts. The compounds may also be used in the form of one of its single enantiomers or alkaline salts thereof.

Some of the above compounds are for instance disclosed in EP-A1-0005129, EP-A1-174726, EP-A1-166287 and GB 2163747.

These active substances are useful for inhibiting gastric acid secretion in mammals and man. In a more general sense, they may be used for prevention and treatment of gastric acid related diseases in mammals and man, including e.g. reflux esophagitis, gastritis, duodenitis, gastric ulcer and duodenal ulcer. Furthermore, they may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. They may also be used in patients in intensive care situations, in patients with acute upper gastrointestinal bleeding, pre-and postoperatively to prevent acid aspiration of gastric add and to prevent and treat stress ulceration. Further, they may be useful in the treatment of psoriasis as well as in the treatment of Helicobacter infections and diseases related to these.

The active compounds are, however, susceptible to degradation/transformation in acidic and neutral media. The degradation is catalyzed by acidic compounds and is stabilized in mixtures with alkaline compounds. The stability of the active substances is also affected by moisture, heat, organic solvents and to some degree by light.

In respect to the stability properties of the active substances, it is obvious that an oral solid dosage form must be protected from contact with the acidic gastric juice and the active substance must be transferred in intact form to that part of the gastrointestinal tract where pH is near neutral and where rapid absorption can occur.

A pharmaceutical oral dosage form of such acid $H^+K^+$-ATPase inhibitors is best protected from contact with acidic gastric juice by an enteric coating layer. In U.S. Pat. No. 4,853,230 such an enteric coated preparation is described. Said preparation contains an alkaline core comprising an acidic susceptible substance, a separating layer and an enteric coating layer. In order to further enhance the stability during storage the prepared formulation may optionally be packed with a desiccant.

There is a demand for development of new enteric coating layered multiple unit preparations with good chemical and mechanical stability making it possible to produce well functioning and patient-friendly packages, such as for instance blister packages. Furthermore, there is a demand for formulations having improved patient acceptance, such as divisible and/or dispersible tablets.

A good mechanical stability can be obtained with an enteric coating layered tablet. WO95/01783 describes such a tablet comprising the acid labile compound omeprazole. However, only an enteric coating layered multiple unit tablet can be made divisible and dispersible. A further advantage of a multiple unit dosage form is that it disperses into a multitude of small units in the stomach upon administration.

Prior art discloses many different types of multiple unit dosage forms. Usually this type of formulation is requested for controlled release formulations, such as sustained release formulations. Typically, the multiple unit formulation may be a tablet which disintegrates in the stomach to make available a multitude of coated units, or pellets filled in a capsule. (See for example EP 0 080 341 and U.S. Pat. No. 4,853,230).

An example to obtain a controlled release dosage form releasing the active substance by diffusion through a membrane is described in U.S. Pat. No. 4,927,640, i.e. a multiple-unit system containing small inert cores coated with active substance and a release controlling polymeric membrane. The mechanical properties of such multiple units formulated into tablets are reported in Pharmaceutical Research 10, (1993), p. S-274. Other examples of controlled release dosage forms are for example described in Aulton M. E. (Churchill Livingstone Ed.), Pharmaceutics: The science of dosage form design (1988), p. 316–321.

Even if there are examples in the prior art mentioning that pellets may be formulated into tablets there are no examples describing any compositions of such a tablet formulation or a technique to manufacture such a formulation of acid labile $H^+K^+$-ATPase inhibitors. In practice, problems arise when enteric coating layered pellets containing acid labile substances are compressed into tablets. If the enteric coating layer does not withstand the compression of the pellets into a tablet the susceptible active substance will be destroyed by penetrating acidic gastric juice, i.e. the acid resistance of the enteric coating layer of the pellets will not be sufficient in the tablet after compression. The above described problems are well illustrated in Reference Examples below.

Further, controlled release tablets from enteric coated particles are described in Drugs Made In Germany, 37 No. 2 (1994), p. 53. The teaching in this reference is that a combination of methacrylic acid copolymer (L30D-55) and a copolymer of ethyl acrylate and methyl methacrylate (NE30D) is suitable as coating polymers for enteric coated particles compressed into tablets. Reference Example III shows that this recommendation is not applicable when formulating multiple unit tableted dosage forms of an acidic susceptible substance such as omeprazole. The acid resistance of the pellets compressed into tablets is too low. The cited reference Drugs Made In Germany also states that the use of the copolymer L30D-55 without the addition of the copolymer NE30D as material for enteric coating layer will result in coated pellets which cannot withstand compression forces used during the tableting process. With reference to this statement it is surprisingly found that pellets covered with L30D55 according to this invention, see Examples, are possible to compress into tablets with fulfilled requirements including acceptable acid resistance of the tablet.

The Applicant is not aware of any working example in the prior art of a multiple unit tableted dosage form comprising an acid labile $H^+K^+$-ATPase inhibitor.

DESCRIPTION OF THE INVENTION

The Applicant has now surprisingly found that tablets according to the present invention comprising enteric coating layered units containing an acid labile $H^+K^+$-ATPase inhibitor or one of its single enantiomers or an alkaline salt thereof can be manufactured by compressing said units into tablets without significantly affecting the properties of the enteric coating layer. As explained above, if the enteric coating layer is damaged during compression of the enteric coating layered units, the acid resistance of said enteric coating layer in the manufactured tablets will not be sufficient and the manufactured tablets will not fulfill standard requirements on enteric coated articles, such as e.g. those defined in the United States Pharmacopeia (USP), hereby incorporated in a whole by reference. Acid labile $H^+K^+$-ATPase inhibitors of interest for the novel dosage form according to the invention are specified in claim 2 and especially preferred compounds are stated in claim 3.

One object of the present invention is to provide a pharmaceutical multiple unit tableted dosage form comprising an add labile $H^+K^+$-ATPase inhibitor or one of its single enantiomers or an alkaline salt thereof, in which the active substance is in the form of individually enteric coating layered units compressed into a tablet. The enteric coating layer(s) covering the individual units of active substance has properties such that the compression of the units into a tablet does not significantly affect the acid resistance of the individually enteric coating layered units. The active substance is prevented from degradation and dissolution in acidic media and has a good stability during long-term storage. The enteric coating layer covering the individual units disintegrates/dissolves rapidly in near neutral or alkaline media.

Another object of the present invention is to provide a pharmaceutical multiple unit tableted dosage form comprising an acid labile $H^+K^+$-ATPase inhibitor or one of its single enantiomers or an alkaline salt thereof which is suitable for press-through blister packages and which also has an improved patient acceptance.

A further object of the present invention is to provide a multiple unit tableted dosage form comprising an acid labile $H^+K^+$-ATPase inhibitor or one of its single enantiomers or an alkaline salt thereof, which is divisible and easy to handle. The multiple unit tableted dosage form may be dispersed in an aqueous liquid and can be given to patients with swallowing disorders and in pediatrics. Such a suspension of dispersed enteric coating layered units of appropriate size can be used for oral administration and also for feeding through a naso-gastric tube.

DETAILED DESCRIPTION OF THE INVENTION

The novel multiple unit tableted dosage form comprising an active substance in the form of an acid labile $H^+K^+$ ATPase inhibitor or one of its single enantiomers or an alkaline salt thereof is characterized in the following way. Individually enteric coating layered units containing active substance and optionally alkaline substances, are mixed with tablet excipients and compressed into multiple unit tableted dosage forms. With the expression "individual units" is meant small beads, particles, granules or pellets, in the following referred to as pellets.

The compaction process (compression) for formulating the multiple unit tableted dosage form must not significantly affect the acid resistance of the enteric coating layered pellets. In other words the mechanical properties, such as the flexibility and hardness as well as the thickness, of the enteric coating layer(s) must secure that the requirements on enteric coated articles in the United States Pharmacopeia are accomplished and that the acid resistance does not decrease more than 10% during the compression of pellets into tablets.

The flexibility/hardness of enteric coating layers can be characterized for instance as Vickers hardness measured with a Shimadzu micro hardness indentation tester type HMV 2 000.

The acid resistance is defined as the amount of active substance in tablets or pellets after being exposed to simulated gastric fluid, USP, or to 0.1M HCl(aq) relative to that of unexposed tablets or pellets, respectively. The test is accomplished in the following way. Tablets or pellets are exposed to simulated gastric fluid at a temperature of 37° C. The tablets disintegrate and release the enteric coating layered pellets to the medium. After two hours the pellets are removed and analyzed for content of active substance using High Performance Liquid Chromatography (HPLC). Present values of acid resistance are averages of at least three individual determinations.

Core material

The core material for the individually enteric coating layered pellets can be constituted according to different principles. Seeds layered with active substance, optionally mixed with alkaline compounds, can be used as the core material for the further processing.

The seeds, which are to be layered with the active substance, can be water insoluble seeds comprising different oxides, celluloses, organic polymers and other materials, alone or in mixtures or water soluble seeds comprising different inorganic salts, sugars, non-pareils and other materials, alone or in mixtures. Further, the seeds may comprise active substance in the form of crystals, agglomerats, compacts etc. The size of the seeds is not essential for the present invention and may vary between approximately 0.1 and 2 mm. The seeds layered with active substance are produced either by powder- or solution/suspension layering using for instance granulating or spray coating/layering equipment.

Before the seeds are layered, the active substance may be mixed with further components. Such components can be binders, surfactants, fillers, disintegrating agents, alkaline additives or other pharmaceutically acceptable ingredients, alone or in mixtures. The binders are for example celluloses such as hydroxypropyl methylcellulose, hydroxypropyl cellulose and carboxymethyl-cellulose sodium, polyvinyl pyrrolidone, sugars, starches and other pharmaceutically acceptable substances with cohesive properties. Suitable surfactants are found in the groups of pharmaceutically acceptable non-ionic or ionic surfactants such as for instance sodium lauryl sulfate.

Alternatively, the $H^+K^+$-ATPase inhibitor or one of its single enantiomers or an alkaline salt thereof, optionally mixed with alkaline compounds and further mixed with suitable constituents can be formulated into core material. Said core materials may be produced by extrusion/ spheronization, balling or compression utilizing different process equipments. The size of the formulated core materials is approximately between 0.1 and 4 mm and preferably between 0.1 and 2 mm. The manufactured core materials can further be layered with additional ingredients comprising active substance and/or be used for further processing.

The active substance is mixed with pharmaceutical constituents to obtain preferred handling and processing properties and a suitable concentration of active substance in the final mixture. Pharmaceutical constituents such as fillers, binders, lubricants, disintegrating agents, surfactants and other pharmaceutically acceptable additives, can be used.

The active substance may also be mixed with an alkaline pharmaceutically acceptable substance (or substances). Such substances can be chosen among, but are not restricted to, substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminium, calcium and magnesium hydroxides; magnesium oxide or composite substances, such as $Al_2O_3 \cdot 6MgO \cdot CO_2 \cdot 12H_2O$, $(Mg_6Al_2(OH)_{16}CO_3 \cdot 4H_2O)$, $MgO \cdot Al_2O_3 \cdot 2SiO_2 \cdot nH_2O$ or similar compounds; organic pH-buffering substances such as trihydroxymethylaminomethane, basic amino acids and their salts or other similar, pharmaceutically acceptable pH-buffering substances.

Alternatively, the aforementioned core material can be prepared by using spray drying or spray congealing technique.

The active substance is in the form of an acid labile $H^+K^+$-ATPase inhibitor according to formula I or one of its single enantiomers or an alkaline salt thereof. These compounds have an asymmetric centre in the sulfur atom, i.e. exists as two optical isomers (enantiomers). Both the pure enantiomers, racemic mixtures (50% of each enantiomer) and unequal mixtures of the two enantiomers are suitable for the pharmaceutical formulation according to the present invention.

Enteric coating layer(s)

Before applying enteric coating layer(s) onto the core material in the form of individual pellets, said pellets may optionally be covered with one or more separating layers comprising pharmaceutical excipients optionally including alkaline compounds such as for instance pH-buffering compounds. This/these separating layer(s) separate(s) the core material from the outer layer(s) being enteric coating layer(s).

The separating layer(s) can be applied to the core material by coating or layering procedures in suitable equipments such as coating pan, coating granulator or in a fluidized bed apparatus using water and/or organic solvents for the coating process. As an alternative the separating layer(s) can be applied to the core material by using powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. Additives such as plasticizers, colorants, pigments, fillers, anti-tacking and antistatic agents, such as for instance magnesium stearate, titanium dioxide, talc and other additives may also be included into the separating layer(s).

When the optional separating layer(s) is applied to the core material it may constitute a variable thickness. The maximum thickness of the optional separating layer(s) is normally only limited by processing conditions. The separating layer(s) may serve as a diffusion barrier and may act as a pH-buffering zone. The pH-buffering properties of the separating layer(s) can be further strengthened by introducing into the layer(s) substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance $Al_2O_3 \cdot 6MgO \cdot CO_2 \cdot 12H_2O$, $(Mg_6Al_2(OH)_{16}CO_3 \cdot 4H_2O)$, $MgO \cdot Al_2O_3 \cdot 2 \cdot nH_2O$, aluminium hydroxide/sodium bicarbonate coprecipitate or similar compounds; or other pharmaceutically acceptable pH-buffering compounds such as, for instance the sodium, potassium, calcium, magnesium and aluminium salts of phosphoric, carbonic, citric or other suitable, weak, inorganic or organic acids; or suitable organic bases, including basic amino acids and salts thereof. Talc or other compounds may be added to increase the thickness of the layer(s) and thereby strengthen the diffusion barrier. The optionally applied separating layer(s) is not essential for the invention. However the separating layer(s) may improve the chemical stability of the active substance and/or the physical properties of the novel multiple unit tableted dosage form.

One or more enteric coating layers are applied onto the core material or onto the core material covered with separating layer(s) by using a suitable coating technique. The enteric coating layer material may be dispersed or dissolved in either water or in suitable organic solvents. As enteric coating layer polymers one or more, separately or in combination, of the following can be used; e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s).

The enteric coating layers contain pharmaceutically acceptable plasticizers to obtain the desired mechanical properties, such as flexibility and hardness of the enteric coating layers. Such plasticizers are for instance, but not restricted to, triacetin, citric acid esters, phthalic acid esters, dibutyl sebacate, cetyl alcohol, polyethylene glycols, polysorbates or other plasticizers.

The amount of plasticizer is optimized for each enteric coating layer formula, in relation to selected enteric coating layer polymer(s), selected plasticizer(s) and the applied amount of said polymer(s), in such a way that the mechanical properties, i.e. flexibility and hardness of the enteric coating layer(s), for instance exemplified as Vickers hardness, are adjusted so that the acid resistance of the pellets covered with enteric coating layer(s) does not decrease significantly during the compression of pellets into tablets. The amount of plasticizer is usually above 10% by weight of the enteric coating layer polymer(s), preferably 15–50% and more preferably 20–50%. Additives such as dispersants, colorants, pigments, polymers e.g. poly (ethylacrylat, methylmethacrylat), anti-tacking and anti-foaming agents may also be included into the enteric coating layer(s). Other compounds may be added to increase film thickness and to decrease diffusion of acidic gastric juices into the acidic susceptible material.

To protect an acidic susceptible substance, such as $H^+K^+$-ATPase inhibitors and to obtain an acceptable acid resistance of the multiple unit tableted dosage form according to the invention, the enteric coating layer(s) constitutes a thickness of approximately at least 10 μm, preferably more than 20 μm. The maximum thickness of the applied enteric coating layer(s) is normally only limited by processing conditions.

Over-coating layer

Pellets covered with enteric coating layer(s) may further be covered with one or more over-coating layer(s). The over-coating layer(s) can be applied to the enteric coating layered pellets by coating or layering procedures in suitable equipments such as coating pan, coating granulator or in a fluidized bed apparatus using water and/or organic solvents for the layering process. The materials for over-coating layers are pharmaceutically acceptable compounds such as, for instance sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives may also be included into the over-coating layer(s). Said over-coating layer may further prevent potential agglomeration of enteric coating layered pellets, protect the enteric coating layer towards cracking during the compaction process and enhance the tableting process. The maximum thickness of the applied over-coating layer(s) is normally only limited by processing conditions.

Tablets

The enteric coating layered pellets are mixed with tablet excipients and compressed into a multiple unit tableted dosage form according to the present invention. The enteric coating layered pellets with or without an over-coating layer are mixed with tablet excipients such as fillers, binders, disintegrants, lubricants and other pharmaceutically acceptable additives and compressed into tablets. The compressed tablet is optionally coated with filmforming agent(s) to obtain a smooth surface of the tablet and further enhance the stability of the tablet during packaging and transport. Such a tablet coating layer may further comprise additives like anti-tacking agents, colorants and pigments or other additives to obtain a tablet of good appearance.

The amount of enteric coating layered pellets constitutes less than 75% by weight of the total tablet weight and preferably less than 60%. By choosing small enteric coating layered pellets in the formulation according to the present invention, the number of pellets in each tablet can be held high, which in turn makes the tablet divisible with retained dosing accuracy.

The mechanical properties, i.e. the flexibility and hardness of the enteric coating layer are essential for the acid resistance of the multiple unit tableted dosage form. The flexibility/hardness of the enteric coating layer surface may be characterized as a preliminary process parameter in the form of Vickers hardness, measured on enteric coating layered pellet(s) before compression of said pellets into tablets. The Vickers hardness may be measured with a Shimadzu micro hardness indentation tester type HMV 2000 (Micro Hardness Testing Machines for Vickers and Knoop Hardness JIS B 7734-1984 and JIS Z 2251-1980). The ability of the enteric coating layer(s) to withstand compression into tablets is, of course, a function of both the amount of applied coating layer and the mechanical properties of said coating layer material. To obtain well functioning enteric coating layered pellets with a reasonable amount of enteric coating layer material by which pellets can be compressed into tablets without significantly affecting the acid resistance, an enteric coating layer surface with a Vickers hardness of less than 8 is preferred. In case the pellets are covered with an over-coating layer the Vickers hardness of the enteric coating layer must be characterized before the over-coating layer is applied. A harder over-coating layer (Vickers hardness higher than 8) can be applied on top of a flexible and softer (Vickers hardness less than 8) enteric coating layer with retained acid resistance during compaction.

Thus, the formulation according to the invention consists of core material containing active substance, optionally mixed with alkaline compound(s), and excipients. The addition of an alkaline material may not be necessary, but such a substance may further enhance the stability of the active substance. The core material is optionally covered with one or more separating layer(s) optionally containing alkaline substance(s). The pellets, optionally covered with a separating layer(s), are then covered with one or more enteric coating layer(s) making the pellets insoluble in acid media, but disintegrating/dissolving in near neutral to alkaline media such as, for instance the liquids present in the proximal part of the small intestine, the site where dissolution is wanted. The enteric coating layered pellets may further be covered with an over-coating layer before being formulated into the multiple unit tableted dosage form.

Process

The process for the manufacture of the dosage form represents a further aspect of the invention. The pharmaceutical processes can preferably be completely water-based and there are different descriptions given in the accompanying examples below.

Use of preparation

The preparation according to the invention is especially advantageous in reducing gastric acid secretion. It is administered one to several times a day. The typical daily dose of the active substance varies and will depend on various factors such as the individual requirements of the patients, the mode of administration and disease. In general the daily dose will be in the range of 1–1000 mg of active substance.

The preparation according to the present invention is also suitable for dispersion in an aqueous liquid with neutral or slightly acidic pH-value before being orally administered or fed through a naso-gastric tube.

The invention is illustrated more in detail by the following examples.

EXAMPLES

Example 1

| Core material | |
|---|---|
| Lansoprazole | 400 g |
| Sugar sphere seeds | 400 g |
| Hydroxypropyl methylcellulose | 82 g |
| Sodium lauryl sulfate | 3 g |
| Purified water | 1600 g |
| Separating layer | |
| Core material | 400 g |
| Hydroxypropyl cellulose | 40 g |
| Talc | 69 g |
| Magnesium stearate | 6 g |
| Purified water | 800 g |

-continued

| Enteric coating layer | |
| --- | --- |
| Pellets covered with separating layer | 400 g |
| Methacrylic acid copolymer | 200 g |
| Triethyl citrate | 60 g |
| Mono- and diglycerides | 10 g |
| Polysorbate 80 | 1 g |
| Purified water | 420 g |
| Tablets | |
| Enteric coating layered pellets | 82 g |
| Microcrystalline cellulose | 191 g |

Suspension layering is performed in a fluid bed apparatus using bottom spray technique. Lansoprazole is sprayed onto sugar sphere seeds from a water suspension containing the dissolved binder. The size of sugar sphere seeds are in the range of 0.25 to 0.35 mm.

The prepared core material is covered with separating layer in a fluid bed apparatus with a hydroxypropyl cellulose solution containing talc and magnesium stearate. The enteric coating layer is sprayed as a water dispersion onto the pellets covered with separating layer in a fluid bed apparatus. Vickers hardness on enteric coating layered pellets is measured to a value of 2.

Enteric coating layered pellets and microcrystalline cellulose are mixed and compressed into tablets using a single punch tableting machine using 10 mm round punches. The upper punch force is set to 5 kN and tablet hardness measured on a Schleuniger hardness tester is 168–185N.

Example 2

| Core material | |
| --- | --- |
| Pantoprazole | 600 g |
| Mannitol | 1000 g |
| Microcrystalline cellulose | 300 g |
| Hydroxypropyl cellulose | 100 g |
| Sodium lauryl sulfate | 6 g |
| Purified water | 802 g |
| Separating layer | |
| Core material | 400 g |
| Hydroxypropyl methylcellulose | 48 g |
| Purified water | 960 g |
| Enteric coating layer | |
| Pellets covered with separating layer | 200 g |
| Methacrylic acid copolymer | 100 g |
| Triethyl citrate | 30 g |
| Mono- and diglycerides | 5 g |
| Polysorbate 80 | 0.5 g |
| Purified water | 309 g |
| Tablets | |
| Enteric coating layered pellets | 200 g |
| Microcrystalline cellulose | 299 g |
| Sodium stearyl fumarate | 1.2 g |

Sodium lauryl sulfate is dissolved in purified water to form the granulation liquid. Pantoprazole, mannitol, microcrystalline cellulose and hydroxypropyl cellulose are dry-mixed. The granulation liquid is added to the powder mixture and the mass is wet-mixed.

The wet mass is forced through an extruder equipped with screens, aperture size 0.5 mm. The extrudate is spheronized on a friction plate in a spheronizing apparatus. The core material is dried in a fluid bed dryer and classified. The prepared core material is covered with separating layer in a fluid bed apparatus with a hydroxypropyl methyl-cellulose/water solution.

The enteric coating layer is applied to the pellets covered with separating layer from an aqueous dispersion of methacrylic acid copolymer plasticized with triethyl citrate to which a mono- and diglycerides/polysorbate dispersion has been added. The pellets are dried in a fluid bed apparatus.

Enteric coating layered pellets, microcrystalline cellulose and sodium stearyl fumarate are mixed and compressed into tablets with a tablet weight corresponding to 20 mg active substance, using a single punch tableting machine equipped with 10 mm round punches.

Example 3

| Core material | |
| --- | --- |
| Pantoprazole | 500 g |
| Sugar sphere seeds | 500 g |
| Hydroxypropyl methylcellulose | 150 g |
| Colloidal silicon dioxide | 3 g |
| Purified water | 1400 g |
| Separating layer | |
| Core material | 500 g |
| Hydroxypropyl cellulose | 40 g |
| Talc | 67 g |
| Magnesium stearate | 6 g |
| Purified water | 800 g |
| Enteric coating layer | |
| Pellets covered with separating layer | 500 g |
| Methacrylic acid copolymer | 200 g |
| Triethyl citrate | 60 g |
| Purified water | 392 g |
| Tablets | |
| Enteric coating layered pellets | 430 g |
| Microcrystalline cellulose | 871 g |
| Sodium stearyl fumarate | 3 g |

Pantoprazole, part of the hydroxypropyl methylcellulose and colloidal silicon dioxide are dry-mixed forming a powder mixture. Sugar sphere seeds (0.25–0.35 mm) are layered with the powder in a centrifugal fluidized coating granulator while spraying a hydroxypropyl methylcellulose solution (6%, w/w).

The prepared core material is dried and covered with separating layer in a centrifugal fluidized coating granulator. A fluid bed apparatus is used for enteric coating layering.

Enteric coating layered pellets and tablet excipients are mixed and compressed into tablets using a rotary tableting machine equipped with 6 pairs of 10 mm round punches. The amount of active substance is approx. 20 mg.

Example 4

| Core material | |
| --- | --- |
| Leminoprazole | 200 g |
| Silicon dioxide seeds | 200 g |
| Hydroxypropyl methylcellulose | 35 g |
| Sodium lauryl sulfate | 2 g |
| Purified water | 700 g |
| Separating layer | |
| Core material | 400 g |
| Hydroxypropyl methylcellulose | 32 g |
| Purified water | 700 g |
| Enteric coating layer | |
| Pellets covered with separating layer | 400 g |
| Methacrylic acid copolymer | 250 g |
| Polyethylene glycol 400 | 50 g |

-continued

| | |
|---|---|
| Mono- and diglycerides | 10 g |
| Polysorbate 80 | 1 g |
| Purified water | 650 g |
| Tablets | |
| Enteric coating layered pellets | 500 g |
| Microcrystalline cellulose | 1496 g |
| Sodium stearyl fumarate | 2 g |

Suspension layering is performed in a fluid bed apparatus. Leminoprazole is sprayed onto the seeds of silicon dioxide (size range 0.15–0.3 mm) from a water suspension containing the dissolved binder and a surface active ingredient.

The prepared core material is covered with separating layer in a fluid bed apparatus using a hydroxypropyl methylcellulose solution. The enteric coating layer material is sprayed as a water dispersion onto pellets in a fluid bed apparatus. Enteric coating layered pellets and the tableting excipients are mixed and compressed into tablets as described in Example 2.

Example 5

| Enteric coating layer | |
|---|---|
| Pellets covered with separating layer (manufacturing and composition as in Example 1) | 500 g |
| Methacrylic acid copolymer | 250 g |
| Polyethylene glycol 6000 | 75 g |
| Mono- and diglycerides | 12.5 g |
| Polysorbate 80 | 1.2 g |
| Purified water | 490 g |
| Tablets | |
| Enteric coating layered pellets | 600 g |
| Microcrystalline cellulose | 1395 g |
| Sodium stearyl fumarate | 5 g |

Enteric coating layered pellets, microcrystalline cellulose and sodium stearyl fumarate are mixed and compressed into tablets as described in Example 3.

Example 6

| Enteric coating layer | |
|---|---|
| Pellets covered with separating layer (manufacturing and composition as in Example 1) | 400 g |
| Hydroxypropyl methylcellulose phthalate | 400 g |
| Dietyl phthalate | 80 g |
| Ethanol | 1600 g |
| Acetone | 4000 g |
| Tablets | |
| Enteric coating layered pellets | 500 g |
| Microcrystalline cellulose | 1500 g |
| Magnesium stearate | 5 g |

Enteric coating layering is performed by spraying a solution in a fluid bed. Enteric coating layered pellets, microcrystalline cellulose and magnesium stearate are mixed and compressed into tablets as described in Example 3.

Example 7

| Core material | |
|---|---|
| Lansoprazole | 400 g |
| Sugar sphere seeds (non-pareils) | 400 g |
| Hydroxypropyl methylcellulose | 80 g |
| Purified water | 1600 g |
| Separating layer | |
| Core material | 800 g |
| Hydroxypropyl cellulose | 80 g |
| Talc | 137 g |
| Magnesium stearate | 11 g |
| Purified water | 1600 g |
| Enteric coating layer | |
| Pellets covered with separating layer | 800 g |
| Methacrylic acid copolymer | 400 g |
| Triethyl citrate | 120 g |
| Mono- and diglycerides | 8 g |
| Polysorbate 80 | 1 g |
| Purified water | 800 g |
| Tablets | |
| Enteric coating layered pellets | 1000 g |
| Dibasic calcium phosphate anhydrous | 1760 g |
| Microcrystalline cellulose | 440 g |
| Magnesium stearate | 16 g |

Suspension layering is performed in a fluid bed apparatus. Lansoprazole is sprayed onto sugar sphere seeds from a water suspension containing the dissolved binder.

The prepared core material is covered with separating layer in a fluid bed with a hydroxypropyl cellulose solution containing talc and magnesium stearate. The enteric coating layer is sprayed as a dispersion onto the pellets covered with separating layer in a fluid bed.

Enteric coating layered pellets, dibasic calcium phosphate anhydrous in granulated form, microcrystalline cellulose and magnesium stearate are mixed and compressed into tablets as described in Example 3. Upper punch force is set to approx 30 kN.

Example 8

| Tablets | |
|---|---|
| Enteric coating layered pellets (manufacturing and composition as in Example 1) | 1.00 kg |
| Microcrystalline cellulose | 1.45 kg |
| Anhydrous lactose | 0.14 kg |
| Starch | 0.23 kg |
| Povidone | 0.18 kg |
| Purified water | 0.836 kg |

Povidone is dissolved in water. Microcrystalline cellulose, anhydrous lactose and starch are dry-mixed. The povidone solution is added while wet-mixing. The wet mass is dried in an oven. The granulated mass is milled using an oscillating granulator.

Enteric coating layered pellets and the prepared granulate are mixed and compressed into engraved and scored tablets using a rotary tableting machine equipped with 16 pairs of oval, 8.5×17 mm, tablet punches.

Example 9

| Over-coating layer | |
|---|---|
| Enteric coating layered pellets (manufacturing and composition as in Example 7) | 400 g |
| Hydroxypropyl methylcellulose | 120 g |
| Purified water | 2280 g |
| Tablets | |
| Over-coating layered pellets | 100 g |
| Microcrystalline cellulose | 233 g |

In a fluid bed apparatus a hydroxypropyl methylcellulose solution is sprayed onto enteric coating layered pellets. The Vickers hardness on the enteric coating layered pellets before applying the over-coating layer is 2 and Vickers hardness measured on the over-coating layered pellets is 11. Pellets covered with over-coating layer are mixed with microcrystalline cellulose and compressed into tablets as in Example 2.

Example 10

| Core material | |
|---|---|
| Pantoprazole | 100 g |
| Sugar sphere seeds | 200 g |
| Hydroxypropyl cellulose | 25 g |
| Purified water | 607 g |
| Separating layer | |
| Core material | 200 g |
| Hydroxypropyl cellulose | 20 g |
| Talc | 34 g |
| Magnesium stearate | 3 g |
| Purified water | 400 g |
| Enteric coating layer | |
| Pellets covered with separating layer | 200 g |
| Methacrylic acid copolymer | 100 g |
| Triethyl citrate | 30 g |
| Mono- and diglycerides | 5 g |
| Polysorbate 80 | 0.5 g |
| Purified water | 282 g |
| Tablets | |
| Enteric coating layered pellets | 100 g |
| Microcrystalline cellulose | 232 g |
| Sodium stearyl fumarate | 1 g |

Suspension layering is performed in a fluid bed apparatus. Pantoprazole is sprayed onto sugar sphere seeds from a water suspension containing the dissolved binder.

The prepared core material is covered with separating layer in a fluid bed apparatus. The enteric coating layer is sprayed as a water dispersion onto the pellets covered with separating layer in a fluid bed apparatus.

Enteric coating layered pellets and tablet excipients are mixed and compressed into tablets weighing approx 600 mg using a single punch tableting machine using 12 mm round punches. The upper punch force is set to 5 kN and tablet hardness measured on a Schleuniger hardness tester is 200–220N.

Example 11

| Enteric coating layer | |
|---|---|
| Core material (no separating layer) | 500 g |
| Methacrylic acid copolymer | 500 g |
| Triethyl citrate | 150 g |
| Mono- and diglycerides | 25 g |
| Polysorbate 80 | 2.5 g |
| Purified water | 978 g |
| Tablets | |
| Enteric coating layered pellets | 800 g |
| Microcrystalline cellulose | 1860 g |
| Sodium stearyl fumarate | 7 g |

Core materials are produced as in Example 1 and in Example 10. Enteric coating layered pellets and tablet excipients are compressed as described in Example 3.

Example 12

| Core material | |
|---|---|
| Pariprazole | 100 g |
| Sugar sphere seeds | 200 g |
| Povidone | 25 g |
| Purified water | 750 g |
| Separating layer | |
| Core material | 100 g |
| Povidone | 5 g |
| Purified water | 150 g |
| Enteric coating layer | |
| Pellets covered with separating layer | 100 g |
| Methacrylic acid copolymer | 50 g |
| Triethyl citrate | 15 g |
| Talc | 15 g |
| Purified water | 125 g |
| Tablets | |
| Enteric coating layered pellets | 125 g |
| Microcrystalline cellulose | 300 g |

Suspension layering is performed in a fluid bed apparatus. Pariprazole is sprayed onto sugar sphere seeds from a water suspension containing the dissolved binder. The prepared core material is covered with separating layer in a fluid bed apparatus. The enteric coating layer is sprayed as a water dispersion onto the pellets covered with separating layer in a fluid bed apparatus. Enteric coating layered pellets and microcrystalline cellulose are mixed and compressed into tablets as described in Example 1.

Example 13

| Enteric coating layer | |
|---|---|
| Pellets covered with separating layer | 200 g |
| Hydroxypropyl methylcellulose acetate succinate | 100 g |
| Triethyl citrate | 30 g |
| Purified water | 309 g |
| Ethanol | 720 g |
| Tablets | |
| Enteric coating layered pellets | 100 g |
| Microcrystalline cellulose | 227 g |
| Crospovidone | 5 g |
| Sodium stearyl fumarate | 1 g |

The pellets covered with separating layer are produced as in Example 7. The enteric coating layer is applied in a fluid bed from a water/ethanol solution. The Vickers hardness on enteric coating layered pellets is measured to a value of 5. Enteric coating layered pellets and tablet excipients are mixed and compressed into tablets as in Example 2.

Example 14

| Enteric coating layer | |
|---|---|
| Pellets covered with separating layer | 200 g |
| Methacrylic acid copolymer | 200 g |
| Triethyl citrate | 60 g |
| Mono- and diglycerides | 10 g |
| Polysorbate 80 | 1 g |
| Purified water | 391 g |
| Over-coating layer | |
| Enteric coating layered pellets | 471 g |
| Hydroxypropyl methylcellulose | 6 g |
| Magnesium stearate | 0.2 g |
| Purified water | 120 g |
| Tablets | |
| Over-coating layered pellets | 140 g |
| Microcrystalline cellulose | 114 g |
| Sodium stearyl fumarate | 0.4 g |

Pellets covered with separating layer are produced according to Example 7. The enteric coating layer and the over-coating layer are sprayed onto pellets in a fluid bed apparatus. Over-coating layered pellets and tablet excipients are compressed using a single punch (round, 12 mm) tableting machine. Upper punch force is set to 6 kN.

Example 15

| Enteric coating layer | |
|---|---|
| Pellets covered with separating layer | 200 g |
| Methacrylic acid copolymer | 40 g |
| Triethyl citrate | 12 g |
| Mono- and diglycerides | 2 g |
| Polysorbate 80 | 0.2 g |
| Purified water | 78 g |
| Over-coating layer | |
| Enteric coating layered pellets | 200 g |
| Hydroxypropyl methylcellulose | 4 g |
| Magnesium stearate | 0.1 g |
| Tablets | |
| Over-coating layered pellets | 69 g |
| Microcrystalline cellulose | 230 g |
| Sodium stearyl fumarate | 0.7 g |

Pellets covered with separating layer are produced according to Example 7. The enteric coating layer and the over-coating layer are sprayed onto pellets in a fluid bed apparatus. The amount of enteric coating layer material used in this example corresponds to an enteric coating layer thickness of approx. 20 μm. Over-coating layered pellets and tablet excipients are compressed using a single punch (round, 10 mm) tableting machine. Tablet weight approx. 330 mg.

Example 16

| Enteric coating layer | |
|---|---|
| Pellets covered with separating layer | 500 g |
| Cellulose acetate phtalate | 375 g |
| Diethyl phthalate | 150 g |
| Acetone | 2000 g |
| Ethanol | 2000 g |
| Tablets | |
| Enteric coating layered pellets | 100 g |
| Microcrystalline cellulose | 300 g |
| Crospovidone | 8 g |
| Sodium stearyl fumarate | 1 g |

The pellets covered with separating layer are produced as in Example 7. The enteric coating layer is applied in a fluid bed from a acetone/ethanol solution. Enteric coating layered pellets and tablet excipients are mixed and compressed into tablets as in Example 2.

The results from tests on acid resistance of the enteric coating layered pellets and the compressed tablets are disclosed in Table I, below.

Table I

| Example No | Acid resistance, pellets (%), | Acid resistance, tablets (%), |
|---|---|---|
| 1 | 100 | 93 |
| 10 | 99 | 93 |

Comments

Surprisingly, the acid resistance, tablets, shows that the enteric coating layer according to the present invention sufficiently withstands compression.

Reference example I

| Tablets | |
|---|---|
| Omeprazole enteric coating layered pellets | 180 g |
| Microcrystalline cellulose | 219 g |
| Sodium stearyl fumarate | 1 g |

Omeprazole pellets from Losec® 40 mg capsules are mixed with microcrystalline cellulose and sodium stearyl fumarate and compressed into tablets using a single punch tableting machine. The Vickers hardness on the enteric coating layered pellets is measured to a value of 22. The tablet tooling is round with a diameter of 10 mm. Punch force is set to 3.7 kN.

Reference example II

| Tablets | |
|---|---|
| Lansoprazole enteric coating layered pellets (content of Lanzo ® 30 mg capsules) | 276 g |
| Microcrystalline cellulose | 644 g |

Lansoprazole pellets are mixed with microcrystalline cellulose and tableted in a single punch tableting machine. The Vickers hardness on enteric coating layered pellets is measured to a value of 18. The tablet tooling is round with a diameter of 12 mm. Punch force is set to 3.6 kN.

Reference example III

| Core material | |
|---|---|
| Magnesium omeprazole | 15.0 kg |
| Sugar sphere seeds | 15.0 kg |
| Hydroxypropyl methylcellulose | 2.25 kg |
| Purified water | 40 kg |

-continued

| Separating layer | |
|---|---|
| Core material | 15.0 kg |
| Hydroxypropyl cellulose | 1.5 kg |
| Talc | 2.57 kg |
| Magnesium stearate | 0.21 kg |
| Purified water | 30 kg |
| Enteric coating layer | |
| Pellets covered with separating layer | 200 g |
| Enteric coating layer material is used as described in Drugs Made In Germany 37, No. 2 (1994), p.53, Table 1, Formulation no. 9. The amount of coating polymer as calculated in above reference is 40% (w/w). | |
| Over-coating layer | |
| Enteric coating layered pellets | 291 g |
| Hydroxypropyl methylcellulose | 4 g |
| Magnesium stearate | 0.2 g |
| Purified water | 80 g |
| Tablets | |
| Over-coating layered pellets | 75 g |
| Microcrystalline cellulose | 174 g |
| Sodium stearyl fumarate | 0.6 g |

Suspension layering is performed in a fluid bed apparatus. Omeprazol magnesium is sprayed onto sugar sphere seeds from a water suspension containing the dissolved binder. The separating layer, enteric coating layer and the over-coating layer are sprayed onto pellets in a fluid bed apparatus. The over-coating layer is applied to prevent sticking of pellets before tableting. Over-coating layered pellets and tablet excipients are tableted as in Example 1. Upper punch force is set to 5 kN.

The results from tests on acid resistance of the enteric coating layered pellets and the compressed tablets are disclosed in Table II, below.

Table II

| Reference example number | Acid resistance pellets (%) | Acid resistance tablets (%) |
|---|---|---|
| I | 97 | 6 |
| II | 98 | 25 |
| III | 98 | 82 |

Comments

As can be seen from the presented data, the enteric coating layer of the products studied, including the two marketed products (Reference examples I and II) do not possess the mechanical properties required to withstand compression into tablets.

What is claimed is:

1. An oral pharmaceutical composition in the form of a multiple unit tablet comprising:

a tablet excipient;

a multiple of a core unit comprising as an active ingredient an acid-labile $H^+K^+$-ATPase inhibitor compound in a neutral form or a salt form, a single enantiomer or an alkaline salt of a single enantiomer;

the core unit being covered with at least one enteric coating layer having mechanical properties so as not to significantly affect the acid resistance of the enteric coating layered unit by compression during tableting.

2. The composition according to claim 1, wherein the active ingredient is a compound of the general formula I or an alkaline salt thereof or one of its single enantiomers or an alkaline salt thereof

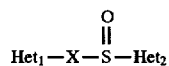

wherein
Het$_1$ is

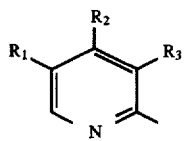 or 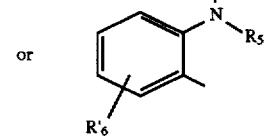

Het$_2$ is

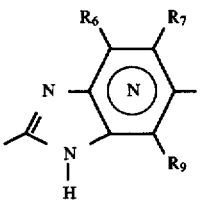 or 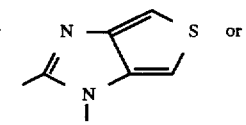 or

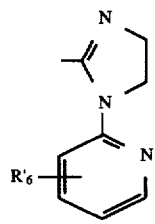

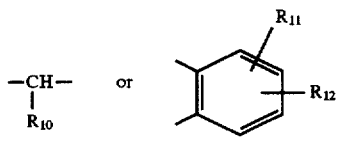

wherein

N in the benzimidazole moiety means that one of the carbon atoms substituted by $R_6$—$R_9$ may be exchanged for a nitrogen atom without any substituents;

R1, R2 and R$_3$ are the same or different and selected from the group consisting of hydrogen, alkyl, alkoxy unsubstituted or substituted by fluorine, alkylthio, alkoxyalkoxy, dialkylamino, piperidino, morpholino, halogen, phenyl and phenylalkoxy;

$R_4$ and $R_5$ are the same or different and selected from the group consisting of hydrogen, alkyl and arylalkyl;

$R'_6$ is hydrogen, halogen, trifluoromethyl, alkyl or alkoxy;

$R_6$—$R_9$ are the same or different and selected from the group consisting of hydrogen, alkyl, alkoxy, halogen, halo-alkoxy, alkylcarbonyl, alkoxycarbonyl, oxazolinyl, trifluoroalkyl, and adjacent groups $R_6$—$R_9$ form ring structures which may be further substituted;

$R_{10}$ is hydrogen or forms an alkylene chain together with $R_3$, and $R_{11}$ and $R_{12}$ are the same or different and selected from the group consisting of hydrogen, halogen and alkyl; except the compounds 5-methoxy-2[[(4-methoxy-3,5-dimethyl-2-pyridinyl)methyl]sulfinyl]-1H-benzimidazole,5-fluoro-2[[(4-cyclopropylmethoxy-2- pyridinyl)methyl]sulfinyl]-1H-benzimidazole and 5-carbomethoxy-6-methyl-2[[(3,4-dimethoxy-2-pyridinyl)methyl]sulfinyl]-1H-benzimidazole or their single enantiomers or alkaline salts thereof.

3. The composition according to claim 1, wherein the active ingredient is one of the following compounds

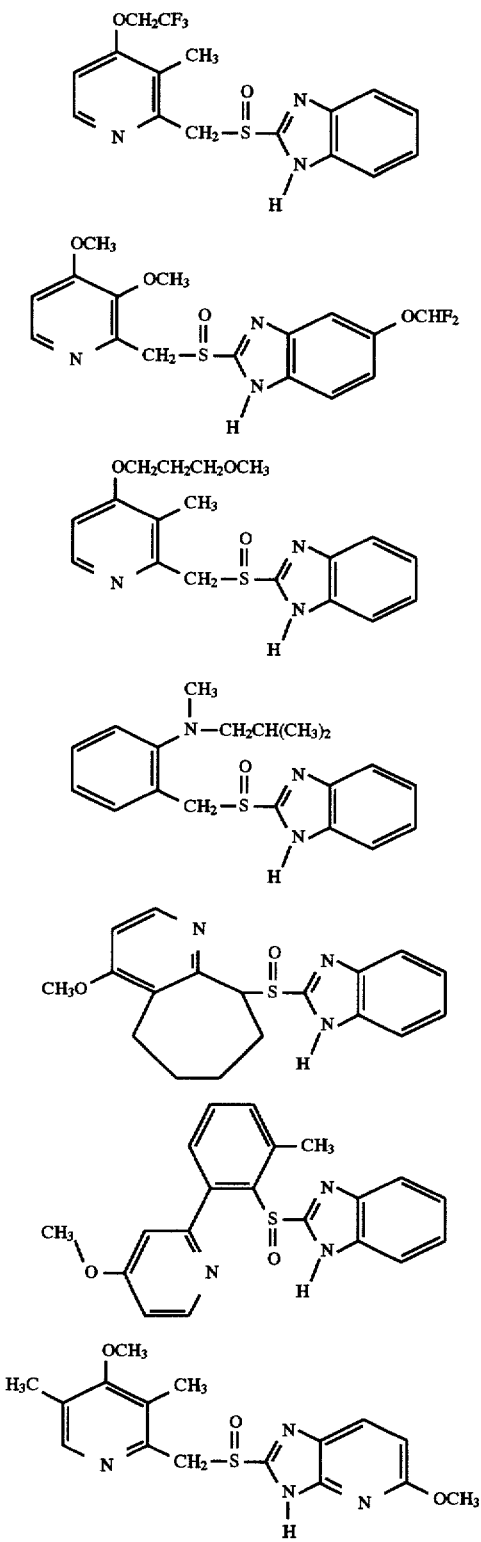
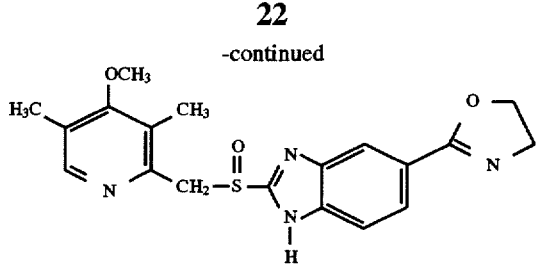

or an alkaline salt thereof or one of its single enantiomers or an alkaline salt thereof.

4. The composition according to claim 1, wherein the acid resistance of the individually enteric coating layered units is in compliance with the requirements on enteric coated articles defined in the United States Pharmacopeia.

5. The composition according to claim 1, wherein the acid resistance of the individually enteric coating layered units does not decrease more than 10% during the compression of the individually enteric coating layered units into the multiple unit tableted dosage form.

6. The composition according to claim 1, wherein the enteric coating layer covering the individual units comprises a plasticized enteric coating layer material.

7. The composition according to claim 1, wherein the enteric coating layer covering the individual units has a thickness of at least 10 µm.

8. The composition according to claim 1, wherein the individually enteric coating layered units are further covered with an over-coating layer comprising pharmaceutically acceptable excipients.

9. The composition according to claim 1, wherein the dosage form is divisible.

10. The composition according to claim 1, wherein the dosage form is dispersible to a suspension of individually enteric coating layered units in an aqueous liquid.

11. The composition according to claim 1 further comprising a separating layer which comprises pharmaceutically acceptable excipients which are soluble, or insoluble but disintegrating in water.

12. The composition according to claim 1, wherein the core unit is a seed layered with the active ingredient.

13. The composition according to claim 12, wherein the seeds have a size of 0.1–2 mm.

14. A process for the manufacture of the pharmaceutical composition according to claim 1, which comprises the steps of (a) shaping a core unit comprising the active ingredient as defined;

(b) covering the core unit with at least one enteric coating layer; and (c) mixing a multiple of the enteric coated core unit with tablet excipients; and (d) compressing a dosage of the mixture into tablet form; the enteric coating layer having mechanical properties so as not to affect the acid resistance of the enteric coated units.

15. A process according to claim 14, wherein the individually enteric coating layered units are further coated with an over-coating layer before compression of the individual units into the multiple unit tableted dosage form.

16. The composition according to claim 1, wherein the core unit comprises an alkaline compound.

17. The composition according to claim 11, wherein the separating layer comprises an alkaline excipient.

18. The process according to claim 14, wherein the individual core unit of step (a) further comprises an alkaline compound.

19. The process according to claim 14, wherein the individual core unit is covered with a separating layer located under the enteric coating layer.

20. A press-through blister package comprising a plurality of press-through blisters each containing the composition according to any of the claims 1 to 16 or 17.

21. A method for inhibiting gastric acid secretion in mammals and man comprising administering to a host in need thereof a therapeutically effective dose of a composition according to any of claims 1–16 or 17.

22. A method for the treatment of gastrointestinal inflammatory disease in mammals and man comprising administering to a host in need thereof a therapeutically effective dose of a composition according to any of the claims 1–16 or 17.

23. A press-through blister package comprising at least one press-through blister: comprising a tableted dosage form of the composition according to any of the claims 1 to 16 or 17.

* * * * *

UNITED STATES PATENT AND TRADEMARK OFFICE
CERTIFICATE OF CORRECTION

PATENT NO. : 5,753,265  
DATED : May 19, 1998  
INVENTOR(S) : Bergstrand, et al.

Page 1 of 4

It is certified that error appears in the above-identified patent and that said Letters Patent is hereby corrected as shown below:

On the title page, Item [56], insert the following:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 0 | 0 | 7 | 2 | 0 | 2 | 1 | 8/82 | EP | | | | |
| | | 8 | 5 | 0 | 1 | 2 | 0 | 7 | 9/84 | WO | | | | |
| | | 0 | 5 | 8 | 7 | 2 | 2 | 0 | 8/93 | EP | | | | |
| | | 0 | 5 | 4 | 1 | 3 | 6 | 9 | 11/92 | EP | | | | |
| | | 2 | 2 | 8 | 5 | 9 | 8 | 9 | 1/95 | GB | | | | |
| | | 9 | 4 | 0 | 3 | 1 | 6 | 0 | 7/93 | WO | | | | |
| | | 0 | 6 | 4 | 8 | 4 | 8 | 7 | 10/94 | EP | | | | |
| | | 0 | 1 | 0 | 8 | 5 | 0 | 4 | 10/83 | EP | | | | |
| | | | | | | | | | | | | | | |

UNITED STATES PATENT AND TRADEMARK OFFICE
CERTIFICATE OF CORRECTION

PATENT NO. : 5,753,265

DATED : May 19, 1998

INVENTOR(S) : Bergstrand, et al.

It is certified that error appears in the above-identified patent and that said Letters Patent is hereby corrected as shown below:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 8 | 5 | 0 | 3 | 4 | 3 | 6 | 2/85 | WO | | | | |
| | | 2 | 0 | 6 | 6 | 0 | 7 | 0 | 12/80 | GB | | | | |
| | | 2 | 1 | 3 | 2 | 8 | 8 | 7 | 11/83 | GB | | | | |
| | | 0 | 1 | 1 | 1 | 1 | 0 | 3 | 10/83 | EP | | | | |
| | | 0 | 0 | 8 | 0 | 3 | 4 | 1 | 11/82 | EP | | | | |
| | | 2 | 0 | 9 | 1 | 0 | 9 | 7 | 11/81 | GB | | | | |
| | | 0 | 1 | 7 | 0 | 7 | 5 | 2 | 12/84 | EP | | | | |
| | | 0 | 0 | 1 | 3 | 5 | 6 | 6 | 1/90 | EP | | | | |
| | | | | | | | | | | | | | | |

UNITED STATES PATENT AND TRADEMARK OFFICE
CERTIFICATE OF CORRECTION

PATENT NO. : 5,753,265
DATED : May 19, 1998
INVENTOR(S) : Bergstrand, et al.

Page 3 of 4

It is certified that error appears in the above-identified patent and that said Letters Patent is hereby corrected as shown below:

FOREIGN PATENT DOCUMENTS

| | | | | | | | | PUBLICATION | COUNTRY OR | | | TRANSLATION | |
|---|---|---|---|---|---|---|---|---|---|---|---|---|---|
| | | | DOCUMENT NUMBER | | | | | DATE | PATENT OFFICE | CLASS | SUBCLASS | YES | NO |
| | | 0 | 1 | 0 | 8 | 2 | 9 | 5 | 10/83 | EP | | | | |
| | | 8 | 7 | 0 | 2 | 2 | 4 | 0 | 9/86 | WO | | | | |
| | | 9 | 3 | 1 | 2 | 7 | 7 | 2 | 12/92 | WO | | | | |
| | | 0 | 3 | 9 | 1 | 5 | 1 | 8 | 2/90 | EP | | | | |
| | | 0 | 0 | 0 | 8 | 7 | 8 | 0 | 8/79 | EP | | | | |
| | | 9 | 5 | 1 | 0 | 2 | 6 | 4 | 4/95 | WO | | | | |
| | | | | | | | | | | | | | | |

UNITED STATES PATENT AND TRADEMARK OFFICE
CERTIFICATE OF CORRECTION

PATENT NO. : 5,753,265
DATED : May 19, 1998
INVENTOR(S) : Bergstrand et al.

It is certified that error appears in the above-indentified patent and that said Letters Patent is hereby corrected as shown below:

Claim 2 at column 20, line 39, insert -- X= -- before the formulae.

Claim 20 at column 23, line 11, delete "claims 1 to 16 or 17" and insert therefor -- claims 1-13, 16 or 17 --.

Claim 21 at column 24, line 2, delete "claims 1 to 16 or 17" and insert therefor -- claims 1-13, 16 or 17 --.

Claim 22 at column 24, lines 6-7, delete "claims 1 to 16 or 17" and insert therefor -- claims 1-13, 16 or 17 --.

Claim 23 at column 24, lines 10-11, delete "claims 1 to 16 or 17" and insert therefor -- claims 1-13, 16 or 17 --.

Signed and Sealed this

Twenty-fifth Day of May, 1999

Attest:

*Attesting Officer*

Q. TODD DICKINSON

*Acting Commissioner of Patents and Trademarks*